(12) United States Patent
Powell et al.

(10) Patent No.: US 8,791,251 B2
(45) Date of Patent: Jul. 29, 2014

(54) NON-IONIC ACID-LABILE SURFACTANTS AND METHODS OF USE

(75) Inventors: Matthew Jacob Powell, Westover, WV (US); Trust T. Razunguzwa, Morgantown, WV (US); Miaosheng Li, Morgantown, WV (US)

(73) Assignee: Protea Biosciences, Inc., Morgantown, WV (US)

( * ) Notice: Subject to any disclaimer, the term of this patent is extended or adjusted under 35 U.S.C. 154(b) by 112 days.

(21) Appl. No.: 13/486,231

(22) Filed: Jun. 1, 2012

(65) Prior Publication Data

US 2012/0309954 A1 Dec. 6, 2012

Related U.S. Application Data

(60) Provisional application No. 61/493,052, filed on Jun. 3, 2011.

(51) Int. Cl.
*C07H 13/12* (2006.01)

(52) U.S. Cl.
USPC .......................................................... 536/29.12

(58) Field of Classification Search
CPC ...................................................... C07H 13/12
USPC ...................................................... 536/29.12
See application file for complete search history.

(56) References Cited

U.S. PATENT DOCUMENTS

| | | | |
|---|---|---|---|
| 3,023,182 | A | 2/1962 | Tanabe et al. |
| 3,647,464 | A | 3/1972 | Smith et al. |
| 4,301,044 | A | 11/1981 | Wentler et al. |
| 5,093,043 | A | 3/1992 | Jakobson et al. |
| 5,264,460 | A | 11/1993 | Jakobson et al. |
| 6,429,200 | B1 | 8/2002 | Monahan et al. |
| 7,022,861 | B1 | 4/2006 | McElhanon et al. |
| 7,074,936 | B2 | 7/2006 | Caprioli et al. |
| 7,091,041 | B2 | 8/2006 | Monahan et al. |
| 7,229,539 | B1 | 6/2007 | Lee et al. |
| 7,351,837 | B1 | 4/2008 | McElhanon et al. |
| 8,013,179 | B2 | 9/2011 | Powell et al. |
| 8,232,423 | B2 | 7/2012 | Powell et al. |
| 8,435,756 | B2 | 5/2013 | Powell et al. |
| 8,445,223 | B2 | 5/2013 | Powell et al. |
| 2004/0152913 | A1 | 8/2004 | Caprioli et al. |
| 2006/0240562 | A1 | 10/2006 | Caprioli et al. |
| 2006/0270584 | A1 | 11/2006 | Frantz et al. |
| 2009/0292136 | A1 | 11/2009 | Powell et al. |
| 2011/0282096 | A1 | 11/2011 | Powell et al. |

FOREIGN PATENT DOCUMENTS

WO  02/097393 A2  12/2002
WO  03/106379 A1  12/2003

OTHER PUBLICATIONS

Haines et al., Journal of Organic Chemistry, 1982, 47(3), pp. 474-482.*

F.L. Van Delft et al., A Sulfitylation-Oxidation Protocol for the Preparation of Sulfates. J. Org. Chem., 2006, 71, pp. 7473-7476.
T. Takeda et al., Synthesis and Properties of Soap Types of Double-Chain Cleavable Surfactants Derived from Pyruvate. J. Oleo Sci., 2004, 53 (2), pp. 89-95.
M. Fung et al., Hybrid Surfactants Containing Separate Hydrocarbon and Fluorocarbon Chains. J. Phys. Chem., 1992, 96, pp. 6738-6742.
M. Iyer et a., Synthesis of pH-Degradable Nonionic Surfactants and Their Applications in Microemulsions. Langmuir 2001, 17, (22), pp. 6816-6821.
D.A. Jaeger et al., Preparation and Characterization of Glycerol-Based Cleavable Surfactants and Derived Vesicles. J. Am. Chem. Soc. 1989, 111, (8), pp. 3001-3006.
D.A. Jaeger et al., Acid-Catalyzed Hydrolysis and Monolayer Properties of Ketal-Based Cleavable Surfactants. Langmuir 1990, 6 (3), pp. 547-554.
D.A. Jaeger et al., Cleavable Quaternary Hydrazinium Surfactants. Langmuir 1998, 14, (7), pp. 1940-1941.
B. Guyot, et al., Esterification of phenolic acids from green coffee with an immobilized lipase from *Candida antarctica* in solvent-free medium. Biotechnology Letters. Jun. 1997, vol. 19, (6), pp. 529-532.
R.M. Caprioli et al., Mass Spectrometry of Intracellular and Membrane Proteins Using Cleavable Detergents. Anal. Chem. 2003, 75, pp. 6642-6647.
Eckert and Liotta, "Designing Smart Surfactants" printed from www.chbe.gatech.edu/eckert/pdf/_surfactant.pdf, Internet site accessed on Dec. 22, 2009, 8 pages.
"Remove detergent from protein samples," printed from www.thermo.com/eThermo/CMA/PDFs/.../articlesFile_6580.pdf, Internet site accessed on Dec. 22, 2009, 2 pages.
"Care and Use Manual" printed from http://www.waters.com/waters/support.htm?locale=en_NG&lid=10008439&cid=511442*type=USRM, Internet site accessed on Dec. 22, 2009, 4 pages.
ProteaseMAX Surfactant, Trypsin Enhancer, printed from www.promega.com/tbs/lb373/tb373.pdf, Internet site accessed on Dec. 22, 2009, 20 pages.
PPS Silent Surfactant, Acid Cleavable Detergent, Use and Storage Instructions printed from www.proteindiscovery.com/downloads/PPS_PI_UseAndStorage.pdf, Internet site accessed on Dec. 22, 2009, 1 page.

*Primary Examiner* — Traviss C McIntosh, III
(74) *Attorney, Agent, or Firm* — Fitch, Even, Tabin & Flannery LLP

(57) ABSTRACT

A compound may generally comprise the formula:

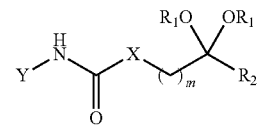

wherein $R_1$ is independently selected from $C_2$-$C_{10}$ alkyl or substituted alkyl, $R_2$ is independently selected from the group consisting of —H and $C_1$-$C_6$ alkyl or substituted alkyl, X is selected from the group consisting of —NH— and —O—, Y is a carbohydrate, and m is an integer from 1 to 8. The compound may comprise a non-ionic acid labile surfactant. The compound may be used to facilitate solubilization of proteins and other molecules in an aqueous environment.

20 Claims, 6 Drawing Sheets

(56) References Cited

OTHER PUBLICATIONS

FAQs about PPS Silent Surfactant, printed from http://www.proteindiscovery.com/pages/support/faq_pps.html, Internet site accessed on Dec. 22, 2009, 2 pages.

RapiGest SF, printed from www.orbital.com.cn/up/Waters%20Science%20Solutions.pdf. Internet site accessed on Dec. 22, 2009, 1 page.

McMillen et al., "Identifying Regions of Membrane Proteins in Contact with Phospholipid Head Groups: Covalent Attachment of a New Class of Aldehyde Lipid Labels to Cytochrome c Oxidase." Biochemistry, 1986, (25) pp. 182-193.

Rouhana et al., "Aggregation-Resistant Water-Soluble Gold Nanoparticles," Langmuir, 2007 (23) pp. 12799-12801.

Regen, Steven L.; Singh, Maninder; Samuel, N. K. P., Functionalized liposomes. Efficient of alpha chymotrypsin, Biochemical and Biophysical Research Communications, (1984), 119(2), pp. 646-651.

* cited by examiner

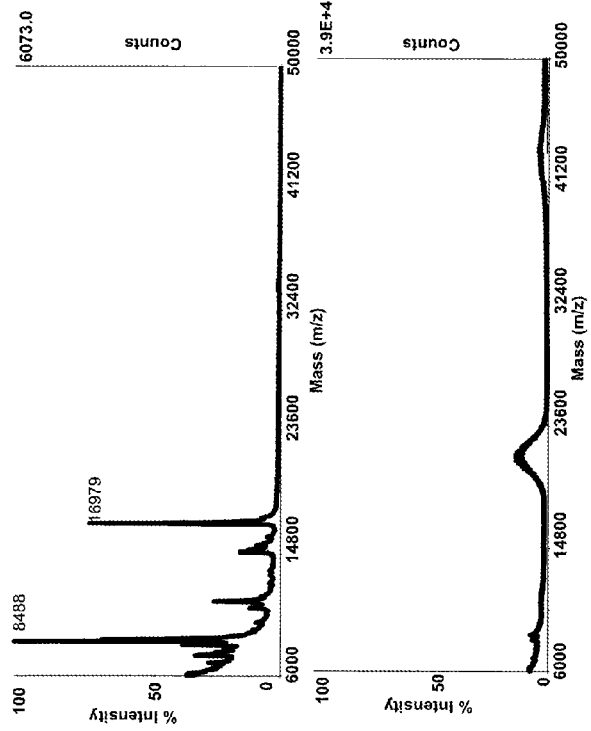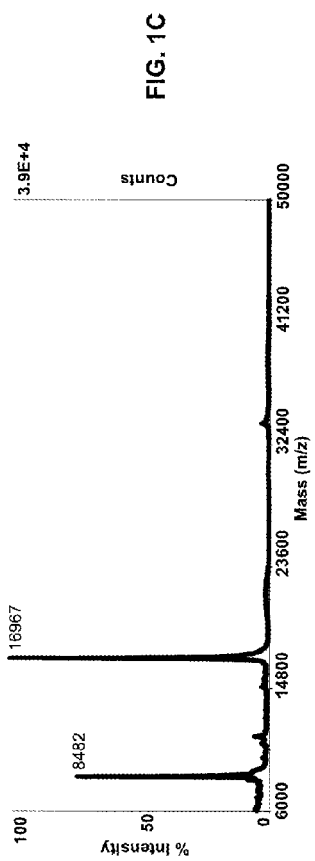

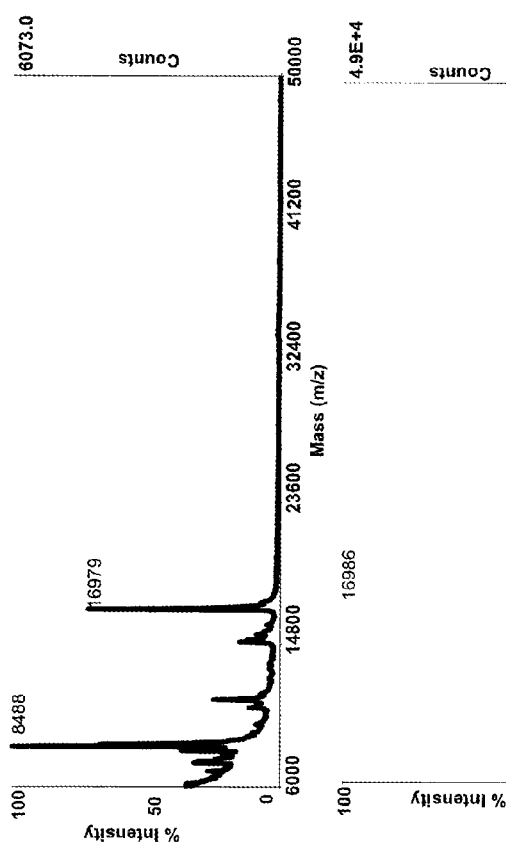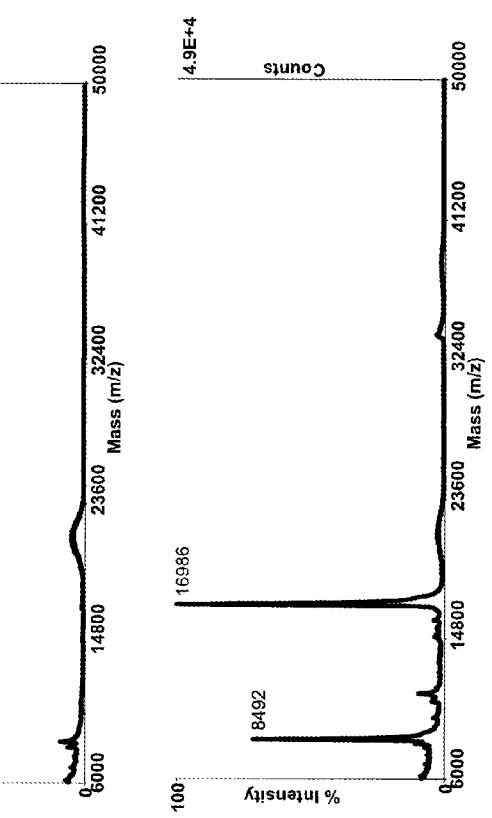

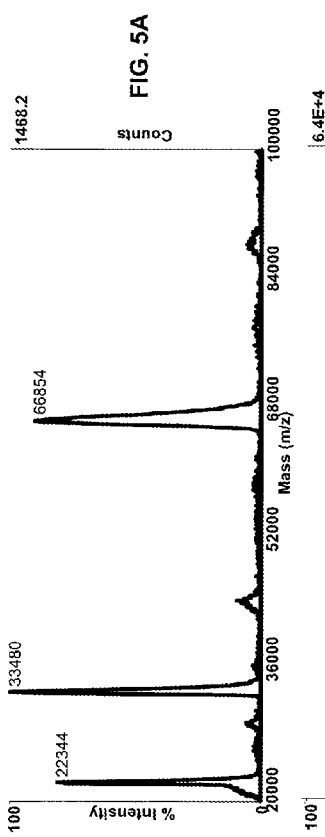
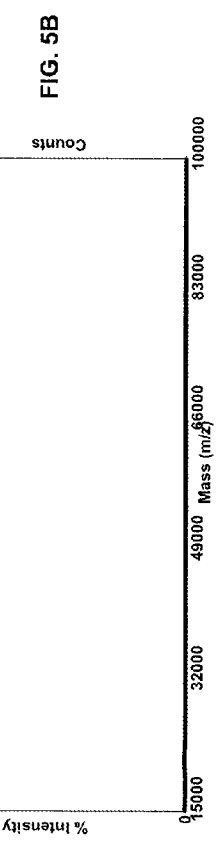
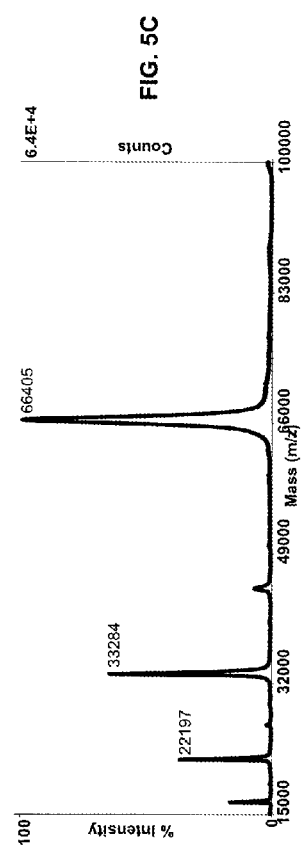

Properties of Acid Labile Non-Ionic Surfactants

| | C5 | C6 |
|---|---|---|
| | $C_{26}H_{50}N_2O_{13}$<br>Exact Mass: 598.331<br>Mol. Wt.: 598.681 | $C_{28}H_{54}N_2O_{13}$<br>Exact Mass: 626.363<br>Mol. Wt.: 626.734 |
| CMC | 4.6 mM | 0.44 mM |
| Solubility in $H_2O$ | Very soluble >2% | Slightly soluble ~0.05% |
| Stability in pure $H_2O$ at RT | Decomposed about 10% in one week | Decomposed about 10% in one week |
| Acid lability in 1% TFA | Decomposed completely in 10 min. | Decomposed completely in 10 min. |

FIG. 6

NON-IONIC ACID-LABILE SURFACTANTS AND METHODS OF USE

CROSS-REFERENCE TO RELATED APPLICATION

This application claims the benefit of U.S. Provisional Application No. 61/493,052, filed on Jun. 3, 2011, which is incorporated herein by reference in its entirety.

BACKGROUND

The compounds and methods described herein generally relate to non-ionic acid-labile surfactants and methods of use.

Proteomics is the study of the structure and function of proteins and other molecules in biological systems. Some purification and identification techniques used in proteomics require the proteins and other molecules to be solubilized in an aqueous environment. Most proteins and other hydrophobic molecules or molecules with significant hydrophobic regions, however, are not readily soluble in an aqueous environment. A surfactant or detergent may generally be used to facilitate the solubilization of proteins and other molecules in an aqueous environment.

Cleavable surfactants have been successfully used to facilitate the solubilization of proteins and other molecules in an aqueous environment. Cleavable surfactants may generally comprise a polar (hydrophilic) group joined by a cleavable linker to a non-polar (hydrophobic) group. Cleavable surfactants may be cleaved or degraded by utilizing acidic conditions, basic conditions, photodegradation, thermal degradation, or chemical reduction. The cleavage by-products may be separated from the proteins or other molecules using standard isolation techniques. Conventional non-ionic cleavable surfactants, however, may generally comprise chemical structures that are complex to synthesize, require harsh conditions (e.g., pH 1-2) or long periods of time (up to several hours) to cleave, and/or generate cleavage by-products that interfere with purification and identification techniques.

Accordingly, more efficient non-ionic cleavable surfactants and methods of use are desirable.

SUMMARY

According to certain embodiments, more efficient non-ionic cleavable surfactants and methods of use are described.

In various embodiments, a compound may generally comprise the formula:

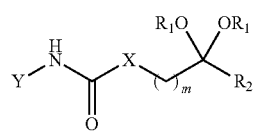

wherein $R_1$ is independently selected from $C_2$-$C_{10}$ alkyl or substituted alkyl, $R_2$ is independently selected from the group consisting of —H and $C_1$-$C_6$ alkyl or substituted alkyl, X is selected from the group consisting of —NH— and —O—, Y is a carbohydrate, and m is an integer from 1 to 8.

DESCRIPTION OF THE DRAWINGS

The various embodiments of non-ionic acid-labile surfactants and methods of use described herein may be better understood by considering the following description in conjunction with the accompanying drawings.

FIGS. 1A-C illustrate representative mass spectra of myoglobin according to certain embodiments.

FIGS. 4A-C illustrate representative mass spectra of myoglobin according to certain embodiments.

FIGS. 5A-C illustrate representative mass spectra of BSA according to certain embodiments.

FIG. 6 includes a chart listing certain properties of certain embodiments.

DESCRIPTION OF CERTAIN EMBODIMENTS

A. Definitions

Figure 2A:
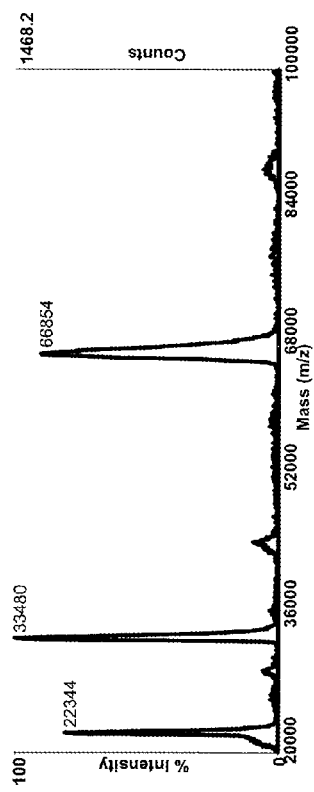
FIGS. 2A-C illustrate representative mass spectra of bovine serum albumin (BSA) according to certain embodiments.

As generally used herein, the term "comprising" refers to various components conjointly employed in the manufacture and use of the compounds and methods described herein. Accordingly, the terms "consisting essentially of" and "consisting of" are embodied in the term "comprising".

As generally used herein, the grammatical articles including "one", "a", "an", and "the" refer to "at least one" or "one or more" of what is claimed or described, unless otherwise indicated. Thus, the articles are used herein to refer to one or more than one (i.e., to at least one) of the grammatical objects of the article. By way of example, "a component" means one or more components, and thus, possibly, more than one component is contemplated and may be employed or used.

As generally used herein, the terms "include", "includes" and "including" are meant to be non-limiting.

As generally used herein, the terms "have", "has" and "having" are meant to be non-limiting.

All numerical quantities or characteristics stated herein are approximate unless otherwise indicated, meaning that all numerical quantities are to be understood as being prefaced and modified in all instances by the term "about". Each numerical quantity is intended to mean both the recited value and a functionally equivalent range surrounding that value unless otherwise indicated. At the very least, and not as an attempt to limit the application of the doctrine of equivalents to the scope of the claims, each numerical parameter described in the present description should at least be construed in light of the number of reported significant digits and by applying ordinary rounding techniques. Notwithstanding the approximations of numerical quantities stated herein, the numerical quantities described in the Examples are reported as precisely as possible.

All numerical ranges stated herein include all sub-ranges subsumed therein. For example, a range of "1 to 10" is intended to include all sub-ranges between and including the recited minimum value of 1 and the recited maximum value of 10, that is, having a minimum value equal to or greater than 1 and a maximum value of equal to or less than 10. Any maximum numerical limitation recited herein is intended to include all lower numerical limitations. Any minimum numerical limitation recited herein is intended to include all higher numerical limitations. Accordingly, Applicants reserve the right to amend this application, including the claims, to expressly recite any sub-range subsumed within the ranges expressly recited herein. All such ranges are intended to be inherently disclosed herein such that amending to expressly recite any such sub-ranges would comply with the requirements of 35 U.S.C. §112, first paragraph, and 35 U.S.C. §132(a).

As generally used herein, the terms "detergent" and "surfactant" refer to compounds and compositions that may facilitate the solubilization of proteins, other hydrophobic molecules, or molecules with significant hydrophobic regions in an aqueous environment.

As generally used herein, the term "cleave" refers to reducing or destroying the detergent properties of the surfactant. In at least one embodiment, the term "cleave" refers to separating the cleavable linker and the polar group and/or non-polar groups. In various embodiments, the term "cleave" refers to degrading or disrupting the bond between the cleavable linker and the polar group and/or non-polar groups.

As generally used herein, the term "labile" refers to the property of a molecule or bond to undergo chemical, physical, or biological change, degradation, or disruption.

As generally used herein, the term "sample-surfactant complex" refers to the molecular complex that may be formed by a surfactant and a sample.

As generally used herein, the term "sample" refers to any molecule that may be used with the non-ionic acid-labile surfactants or methods described herein, such as, for example, but not limited to, hydrophobic molecules, molecules with significant hydrophobic regions, proteins, peptides, polypeptides, polymers, nucleic acids, lipids, lipophilic cellular components, hydrophilic extracellular components, and any combinations thereof.

As generally used herein, when any variable occurs more than one time in a chemical formula, its definition on each occurrence is independent of its definition at every other occurrence.

As generally used herein, a dash ("-") that is not between two letters or symbols is used to indicate a point of attachment for a substituent.

As generally used herein, the term "alkyl" refers to saturated aliphatic groups, including straight-chain alkyl, branched-chain alkyl, straight or branched chain heteroalkyl, cycloalkyl, heterocyclic alkyl, alkyl substituted cycloalkyl groups, and cycloalkyl substituted alkyl groups, including, for example, but not limited to, methyl, ethyl, n-propyl, isopropyl, n-butyl, sec-butyl, t-butyl, pentyl, n-hexyl, and cyclohexyl.

As generally used herein, the notation "n" in reference to an organic group, wherein n is an integer or an integer range, indicates that the group may contain n carbon atoms or that range of carbon atoms per group. The terminology "$C_n$-$C_m$" in reference to an organic group, wherein n and m are each integers, indicates that the group may contain from n carbon atoms to in carbon atoms per group.

Unless otherwise indicated, all compound or composition levels refer to the active portion of that compound or composition, and are exclusive of impurities, for example, residual solvents or by-products, which may be present in commercially available sources of any compounds or compositions.

All percentages and ratios are calculated by weight unless otherwise indicated. All percentages and ratios are calculated based on the total weight of the compound or composition unless otherwise indicated.

This disclosure describes various elements, features, aspects, and advantages of various non-limiting embodiments of non-ionic acid-labile surfactants and methods of use. It is to be understood that certain descriptions of the disclosed embodiments have been simplified to illustrate only those elements, features and aspects that are relevant to a clear understanding of the disclosed embodiments, while eliminating, for purposes of clarity, other elements, features and aspects. Persons having ordinary skill in the art, upon considering the present description of the disclosed embodiments, will recognize that various combinations or sub-combinations of the disclosed embodiments and other elements, features, and/or aspects may be desirable in a particular implementation or application of the disclosed embodiments. However, because such other elements and/or features may be readily ascertained by persons having ordinary skill upon considering the present description of the disclosed embodiments, and are not necessary for a complete understanding of the disclosed embodiments, a description of such elements and/or features is not provided herein. As such, it is to be understood that the description set forth herein is merely exemplary and illustrative of the disclosed embodiments and is not intended to limit the scope of the invention as defined solely by the claims.

B. Overview

In various embodiments, the non-ionic acid-labile surfactants may generally comprise a non-polar (hydrophobic) group joined by a cleavable linker to a polar (hydrophilic) group. In certain embodiments, the non-ionic acid-labile surfactants described herein may comprise two shorter chain hydrophobic tails that individually bind weaker than conventional surfactants, but collectively bind nearly as well. In various embodiments, the interaction between the cleavable linker and the polar group and/or non-polar group may be covalent bonding, non-ionic bonding, hydrogen bonding, or van der Waals bonding. In various embodiments, the non-ionic acid-labile surfactant may be cleavable. In various embodiments, the non-ionic acid-labile surfactant may be labile. In at least one embodiment, the non-ionic acid-labile surfactant may be acid cleavable, i.e., acidic conditions may be used to cleave the bond between the cleavable linker and the polar group and/or non-polar groups. In various embodiments, the non-ionic acid-labile surfactant may be acid cleavable with the proviso that the acid is not a strong acid.

In various embodiments, the non-ionic acid-labile surfactants may be hydrolyzed at a relatively low pH to generate cleavage by-products, including an non-ionic, water-soluble or partially water-soluble compound (e.g., a non-ionic head group) and a neutral, water-soluble or partially water-soluble compound (e.g., short to mid-length alcohols, such as pentanol, hexanol, heptanol, and octanol). These cleavage by-products may be removed from the sample-surfactant complex more readily than the original surfactants because they exhibit reduced, if any, detergent characteristics and/or do not readily bind to the sample. In various embodiments, the cleavage by-products may be washed away by utilizing a solid phase extraction step in which the sample may be bound to the surface of a reversed phase chromatographic bead.

In various embodiments, the polar group and/or non-polar groups may improve the formation of a surfactant-sample complex. In various embodiments, the polar group and/or non-polar groups may improve the solubility of the cleavage by-products. In various embodiments, the cleavage by-products may minimize signal suppression. In various embodiments, the cleavage by-products may have reduced or negligible detergent characteristics. In various embodiments, the cleavage by-products may be removable by standard isolation techniques. In various embodiments, fewer adducts of the sample and non-degraded surfactant may be formed.

The non-ionic acid-labile surfactants described herein may be useful for purification and identification techniques in which conventional cleavage by-products interfere with the purification and identification of the sample. Examples of proteomic purification and identification technologies that may benefit from the non-ionic acid-labile surfactants described herein include, but are not limited to, ion-pair liquid chromatography, liquid chromatography, mass spectrometric detection, liquid-liquid extraction, solid phase extraction, cell lysis, and other technologies that may benefit from the removal of the surfactants after use.

C. Non-Ionic Acid-Labile Surfactants

In certain embodiments, the non-ionic acid-cleavable surfactant may generally comprise a non-ionic acid-cleavable surfactant comprising at least one non-polar group selected from the group consisting of hydrogen, $C_1$-$C_{12}$ alkyl, and substituted $C_1$-$C_{12}$ alkyl; a polar group comprising a non-ionic group; and a cleavable linker comprising a ketal or an acetal.

In certain embodiments, the non-ionic acid-cleavable surfactant may generally comprise a compound of Formula I:

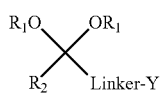

Formula I wherein $R_1$ may be independently selected from the group consisting of hydrogen, $C_1$-$C_{12}$ alkyl, substituted $C_1$-$C_{12}$ alkyl, $R_7$ may be selected from the group consisting of hydrogen, $C_1$-$C_{12}$ alkyl, substituted $C_1$-$C_{12}$ alkyl, Linker may comprise an O-glycosidic linkage, an N-glycosidic linkage, and combinations thereof, and Y may be a carbohydrate. In various embodiments, Y may be selected from the group consisting of monosaccharides, disaccharides, oligosaccharides, polysaccharides, and derivatives thereof. In various embodiments, the Linker may not comprise an O-glycosidic linkage.

In various embodiments, the $R_1$ substituted $C_1$-$C_{12}$ alkyl may be selected from the group consisting of halogen substitution (e.g., —F, —Cl, —Br, or —I substitution), heterocyclic substitution, cyclic alkyl substitution, amide substitution, amine substitution, ester substitution, ether substitution, and phenyl substitution. In various embodiments, $R_1$ substituted $C_1$-$C_{12}$ alkyl may be at least one of fluoralkyl substitution, pre-fluoroalkyl substitution, and benzene substitution.

In various embodiments, the $R_2$ substituted $C_1$-$C_{12}$ alkyl may be selected from the group consisting of alkoxy substitution and halogen substitution (e.g., —F, —Cl, —Br, or —I substitution). In various embodiments, $R_2$ substituted $C_1$-$C_{12}$ alkyl may be at least one of fluoralkyl substitution and pre-fluoroalkyl substitution.

In various embodiments, the Linker may be selected from the group consisting of carbonyl linkage (—C(O)—), an carboalkoxy linkage (—C(O)—O—), a carboxamide linkage (—C(O)—NH—), an amino linkage (—NH—), an amino carboxamide linkage (—NH—C(O)—NH—), and a urethane linkage (—NH—C(O)O—). In various embodiments, the Linker may comprise —NH—C(O)—NH—CH—[CH$_2$—O—C(O)—NH—]$_2$, —NH—C(O)—O—CH—[CH$_2$—O—C(O)—NH—]$_2$, —O—C(O)—NH—CH—[CH$_2$—O—C(O)—NH—]$_2$, —NH—C(O)—NH—C—[CH$_2$—O—C(O)—NH—]$_3$, —NH—C(O)—O—C—[CH$_2$—O—C(O)—NH—]$_3$, and —O—C(O)—NH—C—[CH$_2$—O—C(O)—NH—]$_3$.

In certain embodiments, non-ionic acid-labile surfactants may generally comprise a compound represented by Formula II:

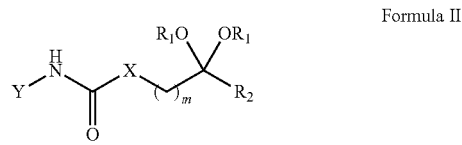

Formula II wherein $R_1$ may be independently selected from $C_2$-$C_{10}$ alkyl or substituted alkyl, $R_2$ may be independently selected from the group consisting of —H and $C_1$-$C_6$ alkyl or substituted alkyl, X may be selected from the group consisting of —NH— and —O—, Y may be a carbohydrate, and m may be an integer from 1 to 8. In various embodiments, the carbohydrate may comprise glucose, galactose, mannose, maltose, and cellobiose. In various embodiments, $R_1$ may be selected from —(CH$_2$)$_{2-7}$CH$_3$ alkyl, $R_2$ may be selected from —(CH$_2$)$_{0-2}$CH$_3$ alkyl, Y may be a sugar, and m may be an integer from 1 to 4. In various embodiments, the sugar may comprise sucrose, lactose and fructose.

In various embodiments, $R_1$ may be selected from —(CH$_2$)$_{2-7}$CH$_3$ alkyl, $R_2$ may be selected from —(CH$_2$)$_{0-2}$CH$_3$ alkyl, Y may be selected from the group consisting of a monosaccharide, a disaccharide, an oligosaccharide, and a polysaccharide, and m may be an integer from 1 to 4. Examples of monosaccharides include, but are not limited to, glucose, galactose, mannose and glucosamine. Examples of disaccharides include, but are not limited to, maltose, cellobiose, lactose, sucrose and fructose. Examples of oligosaccharides include, but are not limited to, two to ten monosaccharide residues, including any of the monosaccharides described herein. Examples of polysaccharides include, but are not limited to, more than ten monosaccharide residues, including any of the monosaccharides described herein. In various embodiments, $R_1$ may be selected from —(CH$_2$)$_{2-7}$CH$_3$ alkyl, $R_2$ may be —CH$_3$, Y may be a disaccharide, and m may be 1. In various embodiments, $R_1$ may be selected from —(CH$_2$)$_{2-7}$CH$_3$ alkyl, $R_2$ may be —CH$_3$, Y may be a trisaccharide, and m may be 1. In various embodiments, $R_1$ may be selected from —(CH$_2$)$_{2-7}$CH$_3$ alkyl, $R_2$ may be —CH$_3$, Y may be a tetrasaccharide, and m may be 1. In various embodiments, $R_1$ may be selected from —(CH$_2$)$_{2-7}$CH$_3$ alkyl, $R_2$ may be —CH$_3$, Y may be a disaccharide comprising a maltose residue, and m may be 1.

In various embodiments, the compound may have a critical micellular concentration (CMC), a solubility in water, a stability in pure water at room temperature, and an acid lability in 1% TFA. In various embodiments, the CMC may be less than 5 mM, less than 1 mM, and less than 0.5 mM. In various embodiments, the CMC may be greater than zero up to 5 mM, greater than zero up to 1 mM, and greater than zero up to 0.5 mM. In various embodiments, solubility in water may be at least 0.05%, greater than 0.1%, greater than 1%, and greater than 2%. In various embodiments, the compound may decompose about 1%, 5%, and 10% in one week in pure water at room temperature. In various embodiments, the compound may decompose 90%, 99%, about 100% and 100% in ten (10) minutes in 1% trifluoroacetic acid (TFA). In various embodiments, the compound may decompose about 100% and 100% in 5 minutes, 10 minutes, and 15 minutes in 1% TFA. As shown in FIG. 6, in at least one embodiment, the CMC may be 4.6 mM, the solubility may be greater than 2%, the compound may decompose about 10% in one week in pure water at room temperature, and the compound may decompose about 100% in ten (10) minutes in 1% TFA. As shown in FIG. 6, in at least one embodiment, the CMC may be 0.44 mM, the solubility in water may be about 0.05%, the compound may decompose about 10% in one week in pure water at room temperature, the compound may decompose about 100% in ten (10) minutes in 1% TFA.

In various embodiments, the compound may comprise N-[2,2-Bis(pentyloxy)propan-1-aminocarbonyl]-β-maltosylamine having the formula:

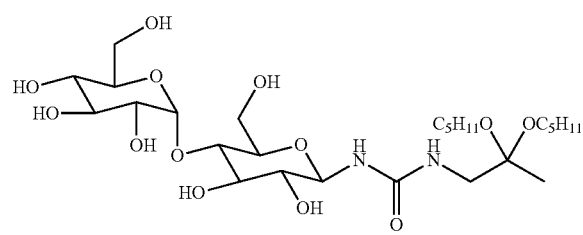

In various embodiments, the compound may comprise N-[2,2-Bis(hexyloxy)propan-1-aminocarbonyl]-β-maltosylamine having the formula:

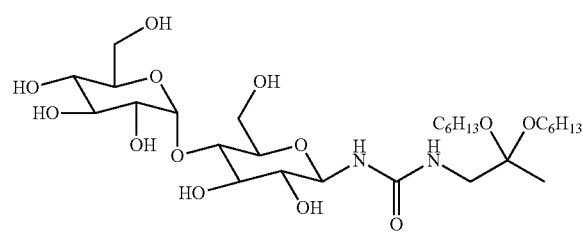

In various embodiments, the compound may comprise N-[2,2-Bis(pentyloxy)propan-1-oxycarbonyl]-β-maltosylamine having the formula:

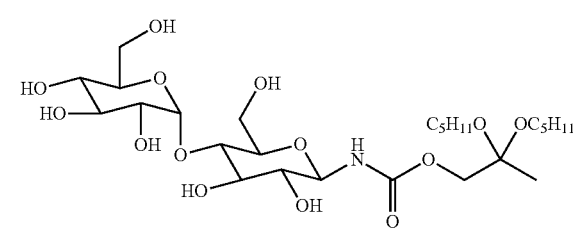

In various embodiments, the compound may comprise N-[2,2-Bis(hexyloxy)propan-1-oxycarbonyl]-β-maltosylamine having the formula:

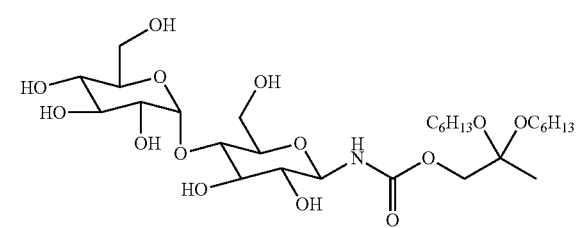

In various embodiments, the compound may comprise the formula:

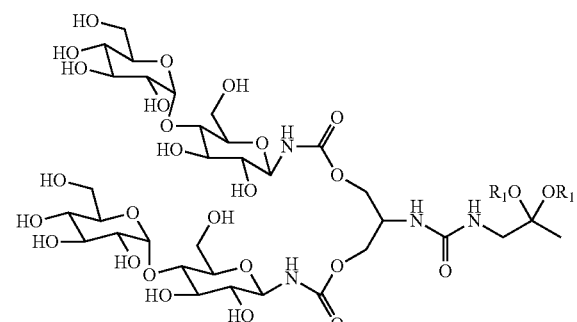

wherein $R_1$ may be independently selected from $C_2$-$C_{10}$ alkyl or substituted alkyl.

In various embodiments, the compound may comprise the formula:

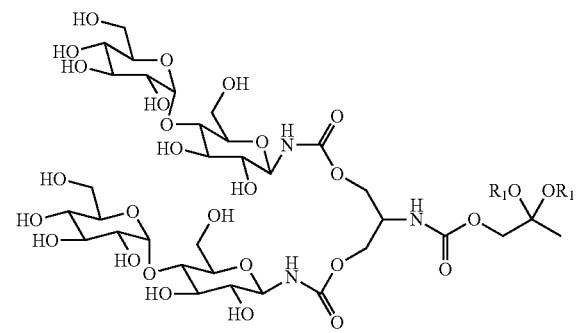

wherein $R_1$ may be independently selected from $C_2$-$C_{10}$ alkyl or substituted alkyl.

In various embodiments, the compound may comprise the formula:

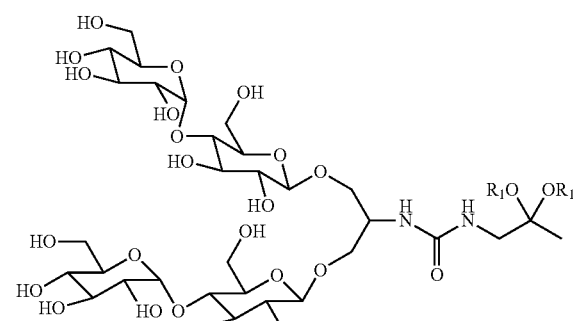

wherein $R_1$ may be independently selected from $C_2$-$C_{10}$ alkyl or substituted alkyl.

In various embodiments, the compound may comprise the formula:

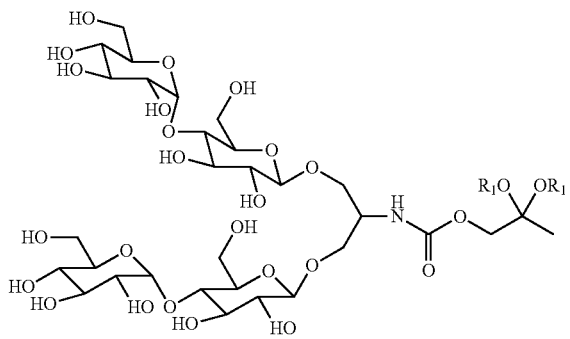

wherein $R_1$ may be independently selected from $C_2$-$C_{10}$ alkyl or substituted alkyl.

In various embodiments, the compound may comprise the formula:

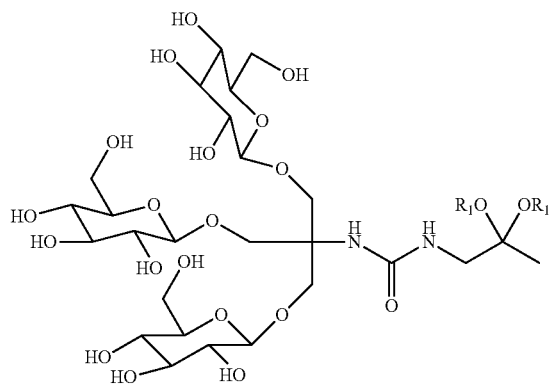

wherein $R_1$ may be independently selected from $C_2$-$C_{10}$ alkyl or substituted alkyl.

In various embodiments, the compound may comprise the formula:

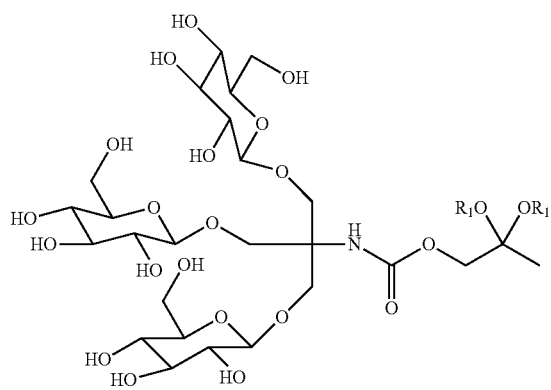

wherein $R_1$ may be independently selected from $C_2$-$C_{10}$ alkyl or substituted alkyl.

In various embodiments, non-ionic acid-labile surfactants may generally comprise a compound represented by Formula II having a rate of degradation of less than 30 minutes. In at least one embodiment, the rate of degradation may be 4-24 minutes. In at least one embodiment, the rate of degradation may be 6-12 minutes. In at least one embodiment, the rate of degradation may be 10 minutes. The rate of degradation generally relates to the rate of how easily the surfactant degrades. Without wishing to be bound to any particular theory, the rate of degradation may depend on the stability of the sample-surfactant complex. The stability of the sample-surfactant complex may depend on the chemical structure of the surfactant and/or the chemical structure of the sample-surfactant complex. For example, the rate of degradation may depend on the electron donating groups and/or electron withdrawing groups.

In certain embodiments, a composition may comprise a sample-surfactant complex. In at least one embodiment, the sample-surfactant complex may generally comprise a sample and a non-ionic acid-labile surfactant according to Formula II. In various embodiments, the composition may comprise a non-ionic acid-labile surfactant according to Formula II and a protein mixture for electrophoresis. Without wishing to be bound to any particular theory, in solution, the hydrophobic tails of the surfactants may associate with the hydrophobic portion of the sample, e.g., proteins, via hydrophobic interactions. The hydrophilic heads of the surfactants may align outwardly from the hydrophobic tails to maximize the distance between the two opposing chemistries, and toward the bulk aqueous solvent where the hydrophilic heads may associate with the polar water molecules. In various embodiments, the sample-surfactant complex may improve the solubility of the native (uncomplexed) sample. In various embodiments, the sample-complex may improve the solubility of the native sample in that the hydrophilic heads provide a cumulative improvement in the soluble nature of the sample-surfactant complex. In various embodiments, the sample-surfactant complex may provide an increased potential for solvation and maintenance of a dissolved state.

D. Synthesis of Various Embodiments

The synthesis of the non-ionic acid-labile surfactant compounds may be carried out using commercially available starting materials. The methods of synthesizing the non-ionic acid-labile surfactants may produce isomers. Although the methods of using the non-ionic acid-labile surfactants may not require separation of these isomers, such separation may be accomplished, if desired, by standard separation methods, such as, for example, preparative high performance liquid chromatography.

The following examples for the preparation of non-ionic acid-labile surfactants are for illustrative purposes, and not intended to limit the scope of the non-ionic acid-labile surfactants compounds and methods described herein. Additionally, in practicing the non-ionic acid-labile surfactants and methods, one of ordinary skill in the art would understand that various modifications to the following procedures would be routine, in light of the teachings herein, and that such modifications would be within the spirit and scope of the non-ionic acid-labile surfactants compounds and methods described herein.

$^1$H NMR and $^{13}$C NMR spectra were recorded on Varian 600 MHz spectrometer. Chemical shifts were reported relative to $CDCl_3$ ($\delta$ 7.24 ppm) or $C_6D_6$ ($\delta$ 7.16 ppm) for $^1$H NMR and $CDCl_3$ ($\delta$ 77.0 ppm) or $C_6D_6$ ($\delta$ 128.4 ppm) for $^{13}$C NMR. Infrared (IR) spectra were obtained on a FT-IR spectrometer. Sorbtech 60A (230-400 mesh) silica gel was used for flash chromatography. Analytical thin-layer chromatography was performed with precoated glass-backed plates (K6F 60 Å, $F_{254}$) and visualized by quenching of fluorescence and by charring after treatment with p-anisaldehyde or phosphomolybdic acid or potassium permanganate stain. $R_f$ values were obtained by elution in the stated solvent ratios (v/v). Ether ($Et_2O$), methylene chloride ($CH_2Cl_2$) and toluene were dried by passing through activated alumina (8×14 mesh) column with argon gas pressure. Commercial reagents were purchased from Fisher Scientific or Sigma-Aldrich and used without purification unless otherwise noted. Air and/or moisture-sensitive reactions were carried out under an atmosphere of argon/nitrogen using oven/flamed-dried glassware and standard syringe/septa techniques. For example, synthetic methods for the preparation of various surfactant compounds may be described in Gerber, S.; Wulf, M.; Milkereit, G.; Vill, V.; Howe, J.; Roessle, M.; Garidel, P.; Gutsmann, T.; Brandenburg, K. *Chem. Phys. Lipids* 2009, 158, 118-130 and Ichikawa, Y.; Matsukawa, Y.; Nishiyama, T.; Isobe, M. *Eur. J. Org. Chem.* 2004, 586-591.

1. 2,2',3,3',4',6,6'-Hepta-O-acetyl-α-maltosyl bromide (2)

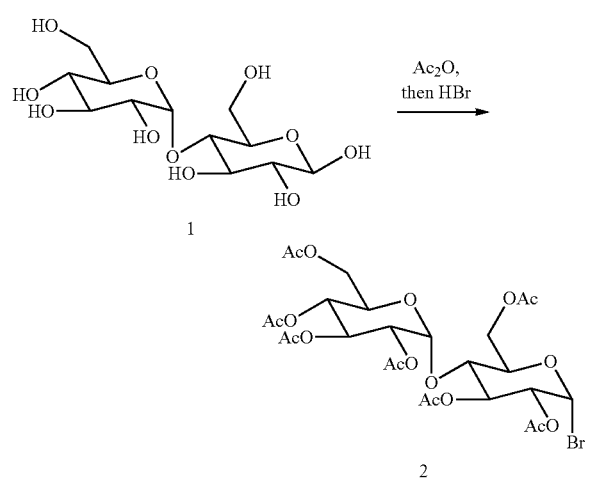

To a suspension of maltose monohydrate 1 (18 g, 50 mmol) in acetic anhydride (70.7 mL, 750 mmol) was added two drops of $HClO_4$ (70%). The mixture was stirred at room temperature for 6 hours and concentrated under vacuum. The resulting octa-O-acetyl-maltose was dissolved in $CH_2Cl_2$ (100 mL) and hydrobromic acid (40 mL, 33% in AcOH) was added to the mixture. The solution was stirred at room temperature for 3 hours and then quenched with ice water (200 mL), and the reaction mixture was extracted with $CH_2Cl_2$ (2×100 mL). The combined organic layers were washed with water (2×100 mL), saturated $NaHCO_3$ (100 mL), brine (100 mL) and dried over anhydrous sodium sulfate. The solvent was removed and the residue was purified by silica gel chromatography (1→40% ethyl acetate/hexane) to give 2,2',3,3',4',6,6'-hepta-O-acetyl-α-maltosyl bromide 2 (25.2 g, 72%) as a light yellow viscous oil: $R_f$ (40% EtOAc/hexane)=0.18; IR (thin film, cm$^{-1}$) 2965, 1742, 1368, 1201, 1030, 912, 731; $^1$H NMR (600 MHz, CDCl$_3$) δ 6.46 (d, J=4.2 Hz, 1H), 5.56 (dd, J=9.6, 9.6 Hz, 1H), 5.37 (d, J=4.2 Hz, 1H), 5.34 (dd, J=10.2, 9.6 Hz, 1H), 5.04 (dd, J=10.2, 9.6 Hz, 1H), 4.83 (dd, J=10.2, 4.2 Hz, 1H), 4.68 (dd, J=10.2, 4.2 Hz, 1H), 4.48 (dd, J=13.8, 3.6 Hz, 1H), 4.23-4.18 (m, 3H), 4.04-3.99 (m, 2H), 3.90 (ddd, J=10.2, 3.0, 3.0 Hz, 1H), 2.10 (s, 3H), 2.05 (s, 3H), 2.03 (s, 3H), 2.02 (s, 3H), 1.99 (s, 3H), 1.98 (s, 3H), 1.96 (s, 3H); $^{13}$C NMR (150 MHz, CDCl$_3$) δ 170.6, 170.4, 170.2, 169.8 (2), 169.4, 169.3, 95.7, 86.0, 72.5, 72.3, 71.5, 70.9, 69.9, 69.2, 68.6, 67.8, 61.8, 61.3, 20.8, 20.7 (2), 20.6 (2), 20.5 (2).

2. 2,2',3,3',4',6,6'-Hepta-O-acetyl-β-maltosyl azide (3)

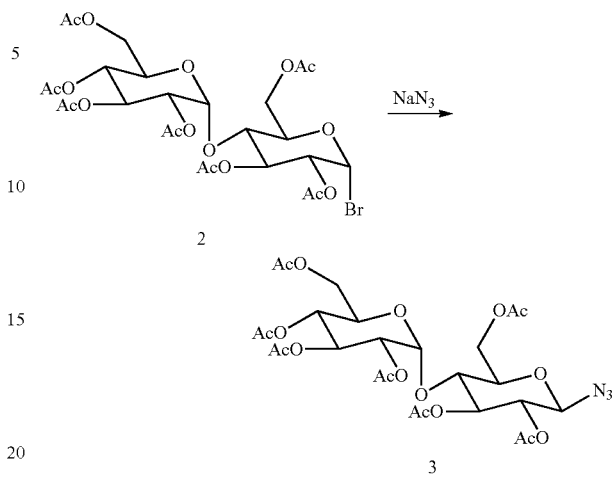

To a solution of bromide 2 (21.5 g, 30.7 mmol) in DMF (50 mL) was added sodium azide (3.0 g, 46 mmol). The solution was stirred at 60° C. for 4 hours. The reaction mixture was cooled to 23° C. and quenched by pouring the mixture into water (200 mL). The mixture was extracted with ethyl acetate (2×100 mL). The combined organic layers were washed with water (2×100 mL), brine (100 mL) and dried over anhydrous sodium sulfate. The solvent was removed and the residue was purified by silica gel chromatography (1-40% ethyl acetate/hexane) to give 2,2',3,3',4',6,6'-hepta-O-acetyl-β-maltosyl azide 3 (17.3 g, 86%) as a colorless viscous oil: $R_f$ (40% EtOAc/hexane)=0.22; IR (thin film, cm$^{-1}$) 2961, 2120, 1742, 1367, 1211, 1029, 914, 732; $^1$H NMR (600 MHz, CDCl$_3$) δ 5.36 (d, J=4.2 Hz, 1H), 5.30 (dd, J=11.2, 9.6 Hz, 1H), 5.21 (dd, J=9.0, 9.0 Hz, 1H), 5.0 (dd, J=11.2, 9.6 Hz, 1H), 4.82 (dd, J=10.8, 4.2 Hz, 1H), 4.74 (dd, J=9.0, 9.0 Hz, 1H), 4.67 (d, J=8.4 Hz, 1H), 4.47 (dd, J=12.0, 3.0 Hz, 1H), 4.21 (d, J=4.2 Hz, 1H), 4.19 (d, J=4.2 Hz, 1H), 4.02-3.95 (m, 2H), 3.92-90 (m, 1H), 3.75-3.73 (m, 1H), 2.11 (s, 3H), 2.06 (s, 3H), 2.00 (s, 3H), 1.99 (s, 3H), 1.98 (s, 3H), 1.96 (s, 3H), 1.95 (s, 3H); $^{13}$C NMR (150 MHz, CDCl$_3$) δ 170.44, 170.42, 170.3, 170.0, 169.8, 169.4, 169.3, 95.6, 87.4, 75.0, 74.2, 72.3, 71.4, 69.9, 69.2, 68.6, 67.9, 62.5, 61.4, 20.8, 20.7, 20.6, 20.5 (2), 20.4 (2).

3. 2,2',3,3',4',6,6'-Hepta-O-acetyl-β-maltosyl amine (4)

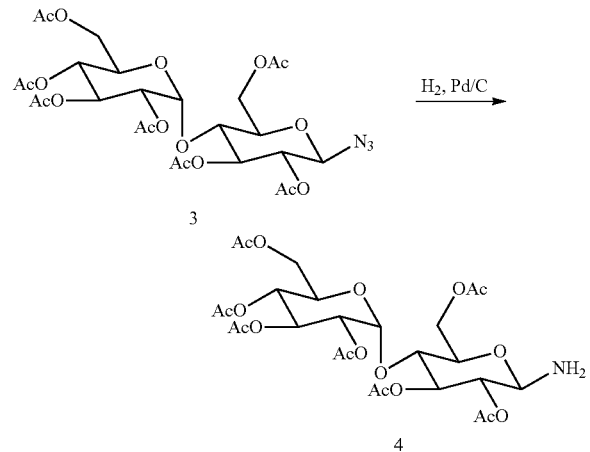

To a solution of the azide 3 (15.8 g, 23.9 mmol) in ethyl acetate (250 mL) was added Pd/C (10%, 0.8 g). The mixture was stirred under hydrogen atmosphere for 5 h. The reaction mixture was filtered through a pad of Celite and concentrated to give 2,2',3,3',4',6,6'-hepta-O-acetyl-β-maltosyl amine 4 (14.3 g, 95%) as a colorless solid: $R_f$ (100% EtOAc/hexane)=0.36; IR (thin film, cm$^{-1}$) 3415, 3347, 2956, 1740, 1368, 1216, 1028, 914, 732; $^1$H NMR (600 MHz, CDCl$_3$) δ 5.37 (d, J=4.2 Hz, 1H), 5.32 (dd, J=10.8, 10.2 Hz, 1H), 5.26 (dd, J=9.0, 9.0 Hz, 1H), 5.02 (dd, J=10.2, 9.6 Hz, 1H), 4.83 (dd, J=10.8, 4.2 Hz, 1H), 4.62 (dd, J=9.6, 9.0 Hz, 1H), 4.43 (dd, J=12.0, 2.4 Hz, 1H), 4.23-4.14 (m, 3H), 4.03 (dd, J=12.0, 2.4 Hz, 1H), 3.94-3.89 (m, 2H), 3.65 (ddd, J=9.6, 4.2, 2.4 Hz, 1H), 2.11 (s, 3H), 2.06 (s, 3H), 2.02 (s, 3H), 2.00 (s, 3H), 1.98 (s, 3H), 1.97 (s, 3H), 1.96 (s, 3H), 1.90 (d, br, J=8.4 Hz, 2H); $^{13}$C NMR (150 MHz, CDCl$_3$) δ 170.6, 170.5 (2), 170.3, 170.0, 169.9, 169.4, 95.4, 84.4, 75.6, 73.0, 72.9, 72.8, 69.9, 69.3, 68.4, 68.0, 63.1, 61.4, 20.9 (2), 20.8, 20.7, 20.6, 20.5 (2).

4. 2,2',3,3',4',6,6'-Hepta-O-acetyl-β-maltosyl isocyanate (5)

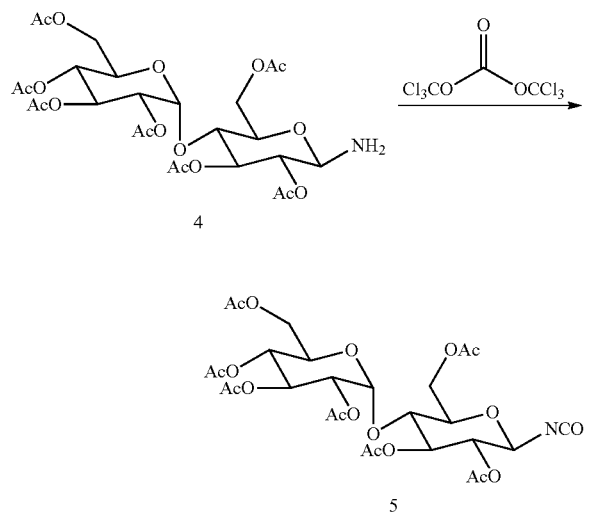

To a stirring mixture of maltosyl amine 4 (12.2 g, 19.2 mmol) in CH$_2$Cl$_2$ (200 mL) and saturated NaHCO$_3$ (120 mL) at 0° C. was added triphosgene (5.7 g, 19.2 mmol). The heterogeneous mixture was stirred for 30 min and diluted with CH$_2$Cl$_2$ (100 mL) and the organic phase was separated without agitation. The organic phase was washed with brine (100 mL) and dried over anhydrous sodium sulfate. After addition of toluene (20 mL), CH$_2$Cl$_2$ was removed to give the toluene solution, from which crystallization was accomplished upon addition of n-hexane (30 mL) at room temperature to yield 2,2',3,3',4',6,6'-hepta-O-acetyl-β-maltosyl isocyanate 5 (9.8 g, 78%) as a colorless solid: $R_f$ (40% EtOAc/hexane)=0.23; IR (thin film, cm$^{-1}$) 2961, 2255, 1743, 1367, 1212, 1028, 912, 730; $^1$H NMR (600 MHz, CDCl$_3$) δ 5.38 (d, J=4.2 Hz, 1H), 5.33 (dd, J=10.8, 9.6 Hz, 1H), 5.20 (m, 1H), 5.04 (dd, J=10.2, 9.6 Hz, 1H), 4.83 (dd, J=10.8, 4.8 Hz, 1H), 4.77-4.74 (m, 2H), 4.48 (dd, J=12.6, 2.4 Hz, 1H), 4.24-4.21 (m, 2H), 4.05-3.98 (m, 2H), 3.95-3.91 (m, 1H), 3.72 (ddd, J=9.6, 4.2, 2.4 Hz, 1H), 2.13 (s, 3H), 2.08 (s, 3H), 2.02 (s, 3H), 2.01 (s, 3H), 2.00 (s, 6H), 1.98 (s, 3H); $^{13}$C NMR (150 MHz, CDCl$_3$) δ 170.7 (2), 170.6, 170.4, 170.1, 169.7, 169.6, 137.8, 95.9, 83.9, 75.7, 74.4, 73.3, 72.7, 70.2, 69.5, 68.8, 68.2, 62.7, 61.7, 60.6, 21.1, 21.0, 20.9, 20.8 (2), 20.7 (2).

5. 2,2-Bis(hexyloxy)propanamide (7)

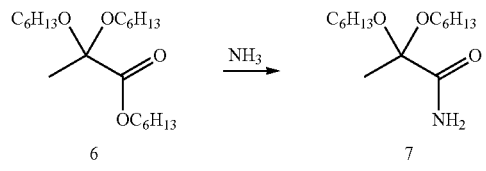

To a solution of ester 6 (22.8 g, 63.6 mmol) in THF (60 mL) was added a solution of dimethyl amine in THF (60 mL, 2M, 120 mmol). The solution was refluxed for 24 h in a pressure tube. The solvent was removed and the residue purified by silica gel chromatography (20→60% ethyl acetate/hexane) to Live 2,2-bis(hexyloxy)propanamide 7 (13.1 g, 76%) as a colorless oil: $R_f$ (15% EtOAc/hexane)=0.36; IR (thin film, cm$^{-1}$) 3485, 3282, 2930, 2858, 1697, 1583, 1457, 1367, 1164, 1135, 1063; $^1$H NMR (600 MHz, CDCl$_3$) δ 6.69 (s, br, 1H), 5.86 (s, br, 1H), 3.45-3.37 (m, 4H), 1.58-1.53 (m, 4H), 1.48 (s, 3H), 1.35-1.24 (m, 12H), 0.86 (t, J=7.2 Hz, 3H); $^{13}$C NMR (150 MHz, CDCl$_3$) δ 173.2, 99.8, 62.3 (t), 31.6, 29.7, 25.9, 22.6, 21.8 (d), 14.0 (d).

2,2-Bis(hexyloxy)propan-1-amine (8)

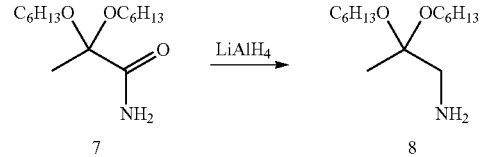

To a mixture of LiAlH$_4$ (2.9 g, 77.6 mmol) in Et$_2$O (150 mL) was added a solution of ester 3 (10.6 g, 38.8 mmol) in Et$_2$O (50 mL). After addition, the mixture was refluxed for 12 hours. The reaction mixture was cooled to 0° C. and quenched with ethyl acetate (20 mL) and H$_2$O (20 mL). The mixture was added saturated potassium sodium tartrate (200 mL) and stirred at 23° C. for 12 hours. The mixture was extracted with Et$_2$O (2×200 mL) and the combined organic layers were dried over anhydrous sodium sulfate. The solvent was removed and the residue was purified by silica gel chromatography (10→20% ethyl acetate/hexane+1% Et$_3$N) to give 2,2-bis (hexyloxy)propan-1-amine 8 (8.1 g, 81%) as a colorless oil: $R_f$ (10% MeOH/EtOAc)=3.0; IR (thin film, cm$^{-1}$) 2929, 2860, 1738, 1467, 1377, 1216, 1082, 954; $^1$H NMR (600 MHz, CDCl$_3$) δ 3.39-3.31 (m, 4H), 2.70 (s, 2H), 1.52-1.46 (m, 4H), 1.32-1.22 (m, 12H), 1.28 (s, 3H), 0.86 (t, J=7.2 Hz, 3H); $^{13}$C NMR (150 MHz, CDCl$_3$) δ 101.2, 60.6, 47.3, 31.7, 30.0, 26.0, 22.6, 20.4, 14.0.

7. 2,2',3,3',4',6,6'-Hepta-O-acetyl-N-[2,2-bis(hexyloxy)propan-1-aminocarbonyl]-β-maltosylamine (9)

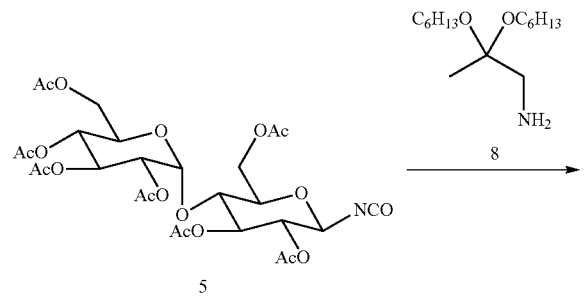

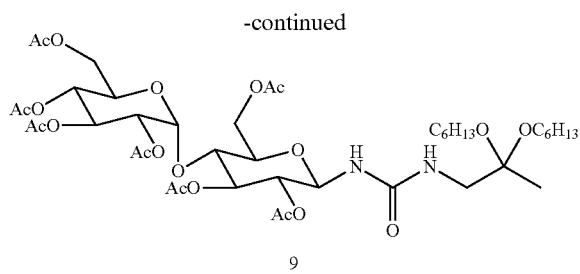

9

To a solution of isocyanate 5 (6.8 g, 10.3 mmol) in CH₂Cl₂ (20 mL) was added amine 8 (2.9 g, 11.2 mmol). The solution was stirred at 23° C. for 10 hours. The solvent was removed and the residue was purified by silica gel chromatography (10→50% ethyl acetate/hexane) to give 2,2',3,3',4',6,6'-Hepta-O-acetyl-N-[2,2-bis(hexyloxy)propan-1-aminocarbonyl]-β-maltosylamine 9 (7.5 g, 80%) as a colorless oil: $R_f$ (60% EtOAc/hexane)=0.38; IR (thin film, cm$^{-1}$) 3364, 2933, 2873, 1746, 1655, 1564, 1367, 1218, 1029, 732; $^1$H NMR (600 MHz, CDCl₃) δ 5.35-5.30 (m, 3H), 5.12 (dd, J=9.6, 9.6 Hz, 1H), 5.02 (dd, J=10.2, 9.6 Hz, 1H), 4.83 (dd, J=10.8, 4.2 Hz, 1H), 4.70 (dd, J=9.6, 9.6 Hz, 1H), 4.38 (dd, J=12.6, 2.4 Hz, 1H), 4.23 (dd, J=12.6, 4.2 Hz, 1H), 4.20 (dd, J=12.6, 4.2 Hz, 1H), 4.02 (dd, J=12.6, 2.4 Hz, 1H), 3.94 (dd, J=9.6, 9.0 Hz, 1H), 3.90 (ddd, J=11.2, 3.0, 3.0 Hz, 1H), 3.76 (ddd, J=9.6, 4.2, 3.0 Hz, 1H), 3.40-3.27 (m, 6H), 3.24 (s, br, 1H), 2.09 (s, 3H), 2.06 (s, 3H), 2.03 (s, 3H), 1.98 (s, 3H), 1.98 (s, 3H), 1.97 (s, 3H), 1.96 (s, 3H), 1.49-1.47 (m, 4H), 1.30-1.26 (m, 12H), 1.23 (s, 3H), 0.86-0.84 (m, 6H); $^{13}$C NMR (150 MHz, CDCl₃) δ 171.0, 170.6, 170.5, 170.4, 169.8, 169.6, 169.4, 158.0, 100.0, 95.5, 79.8, 75.2, 73.5, 72.8, 71.3, 69.9, 69.3, 68.5, 67.9, 62.9, 61.4, 60.9, 60.6, 31.7, 31.6, 30.0, 29.9, 29.8, 26.0, 25.9, 25.9, 22.6, 20.9, 20.9, 20.8, 20.8, 20.6, 20.6, 20.5, 14.0.

8. N-[2,2-Bis(hexyloxy)propan-1-aminocarbonyl]-β-maltosylamine (10).

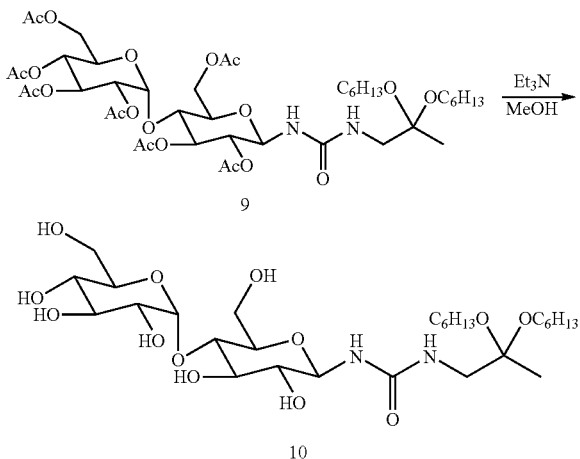

To a solution of ester 9 (5.8 g, 6.3 mmol) in methanol (30 mL) was added Et₃N (3 mL). The solution was stirred at 23° C. for 18 hours. The solution was kept at −20° C. for 24 hours to form a precipitation, which was isolated to give N-[2,2-bis(hexyloxy)propan-1-aminocarbonyl]-β-maltosylamine 10 (2.8 g, 73%) as a colorless solid: $R_f$=N/A; IR (thin film, cm$^{-1}$) 3354, 2930, 1658, 1570, 1025; $^1$H NMR (600 MHz, DMSO-$d_6$+1% D₂O) δ 5.02 (d, J=4.2 Hz, 1H), 4.57 (d, J=9.0 Hz, 1H), 3.65 (dd, J=10.8, 10.8 Hz, 1H), 3.61 (dd, J=10.2, 10.2 Hz, 1H), 3.51-3.42 (m, 4H), 3.38 (dd, J=9.6, 9.0 Hz, 1H), 3.33-3.22 (m, 7H), 3.14-3.04 (m, 3H), 3.00 (dd, J=9.0, 9.0 Hz, 1H), 1.44-1.42 (m, 4H), 1.24-1.22 (m, 12H), 1.13 (s, 3H), 0.82 (t, J=7.2 Hz, 6H); $^{13}$C NMR (150 MHz, DMSO-$d_6$+1% D₂O) δ 158.4, 101.2, 101.1, 100.7, 81.6, 79.8, 77.7, 76.6, 73.8, 73.6, 72.8, 70.3, 61.3, 61.1, 60.6, 44.5, 29.7, 28.6, 22.6, 21.5, 21.4, 14.51, 14.52.

9. 2,2',3,3',4',6,6'-Hepta-O-acetyl-N-[2,2-bis(hexyloxy)propan-1-oxycarbonyl]-β-maltosylamine (12)

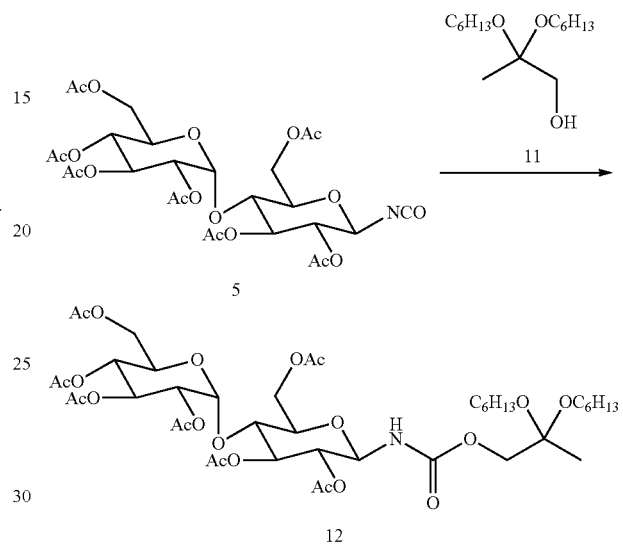

To a solution of isocyanate 5 (1.46 g, 2.2 mmol) in toluene (10 mL) was added alcohol 11 (286 mg, 1.1 mmol). The solution was stirred at 110° C. for 3 hours. The solvent was removed and the residue was purified by silica gel chromatography (10→50% ethyl acetate/hexane) to give 2,2',3,3',4',6,6'-Hepta-O-acetyl-N-[2,2-bis(hexyloxy)propan-1-oxycarbonyl]-β-maltosylamine 12 (780 mg, 77%) as a colorless oil.

10. N-[2,2-Bis(hexyloxy)propan-1-oxycarbonyl]-β-maltosylamine (13)

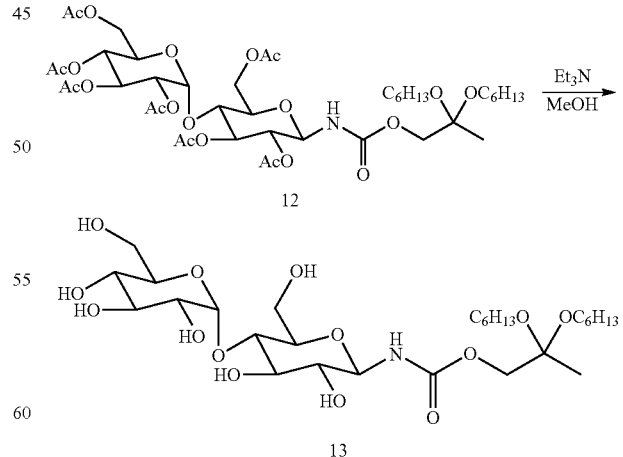

To a solution of ester 12 (530 mg, 0.57 mmol) in methanol (6 mL) was added Et₃N (0.6 mL). The solution was stirred at 23° C. for 18 hours. The solution was kept at −20° C. for 24 hours to form a precipitation, which was isolated to give N-[2,2-bis(hexyloxy)propan-1-oxycarbonyl]-β-maltosylamine 13 (256 mg, 71%) as a colorless solid.

E. Uses for Various Compounds

In various embodiments, the non-ionic acid-labile surfactants may be used to facilitate the solubilization of proteins and other molecules in an aqueous environment. In various embodiments, the non-ionic acid-labile surfactants may be used in purification and identification technologies including, but are not limited to, ion-pair liquid chromatography, liquid chromatography, mass spectrometry (ESI MS and MALDI MS), liquid-liquid extraction, solid phase extraction, HPLC/MS, HPLC/UV analyses and other techniques that benefit from the removal of the non-ionic surfactant after use. In various embodiments, the non-ionic acid-labile surfactants may be used in electrophoresis, capillary electrophoresis, electroelution, cell lysis and protein extraction from cell lines, tissues, and biological samples, selective protein extraction from biological samples, extraction of biomolecules from environmental samples, enzymatic digestion of proteins, disruption of protein-protein interactions, and protein denaturation.

In certain embodiments, a method of isolating a sample may generally comprise adjusting the sample to pH 6-12; mixing a solvent and a non-ionic acid-labile surfactant according to Formula II; contacting the sample with the mixture to form a sample-surfactant complex; cleaving the surfactant from the sample-surfactant complex to form cleavage by-products; and isolating the sample from the cleavage by-products. In various embodiments, the method of isolating a sample may comprise agitating at least one of the sample, mixture, and sample-surfactant complex. In various embodiments, agitating may comprise sonication. In various embodiments, the method of isolating a sample may comprise sonicating the sample-surfactant complex. In various embodiments, the method of isolating a sample may comprise performing mass spectrometry on the isolated sample. In various embodiments, the cleavage by-products may be soluble in at least one of the cleaved sample-surfactant complex. In various embodiments, the cleavage by-products may be soluble in the isolated sample.

In various embodiments, the solvent may be selected from the group consisting of water; 0-50% methanol; 0-70% acetonitrile; 5-50 mM ammonium bicarbonate buffer; 5-50 mM Tris-HCl buffer; 5-50 mM sodium phosphate buffer, 5-50 mM ammonium acetate buffer, and any combination thereof.

In various embodiments, 25 mg of N-[2,2-Bis(pentyloxy) propan-1-oxycarbonyl]-β-maltosylamine may be dissolved in 200 μL of 70% acetonitrile aqueous solution, and diluted with water to a desired concentration. In various embodiments, 10 mg of N-[2,2-Bis(hexyloxy)propan-1-oxycarbonyl]-β-maltosylamine may be dissolved in 200 μL of 70% acetonitrile aqueous solution, and diluted with water to a desired concentration.

In various embodiments, adjusting the sample to pH 6-12 may comprise contacting the sample with an acid or a base. In various embodiments, adjusting the sample to pH 6-12 may comprise contacting the sample with an acid with the proviso that the acid is not a strong acid. In various embodiments, adjusting the sample to pH 6-12 may comprise contacting the sample with a weak acid. In various embodiments, the acid may be selected from the group consisting of formic acid, acetic acid, trifluoroacetic acid, heptafluorobutyric acid, citric acid, phosphoric acid, and boric acid. In various embodiments, the base may be selected from the group consisting of ammonium hydroxide, sodium hydroxide, and potassium hydroxide.

In various embodiments, cleaving may comprise adjusting the sample-surfactant complex to pH 2-3. In various embodiments, adjusting to pH 2-3 may comprise contacting the sample-surfactant complex with an acid. In various embodiments, the adjusting to pH 2-3 may comprise contacting the sample-surfactant complex with an acid with the proviso that the acid in not a strong acid. In various embodiments, adjusting to pH 2-3 may comprise contacting the sample-surfactant complex with a weak acid. In various embodiments, the acid may be selected from the group consisting of formic acid, trifluoroacetic acid, heptafluorobutyric acid, and acetic acid.

In various embodiments, cleaving may comprise incubating the sample-surfactant complex. In at least one embodiment, cleaving may comprise incubating the sample-surfactant complex for less than four (4) hours at less than 99° C. In at least one embodiment, cleaving may comprise incubating the sample-surfactant complex from 5 minutes to 1 (one) hour. In at least one embodiment, cleaving may comprise incubating the sample-surfactant complex from 4-50° C. In at least one embodiment, cleaving may comprise incubating the sample-surfactant complex from 4° C. to room temperature. In at least one embodiment, cleaving may comprise incubating the sample-surfactant complex for 10-30 minutes at 4-50° C. In at least one embodiment, cleaving may comprise incubating for 10 minutes at room temperature.

In various embodiments, isolating the sample from the cleavage by-products may comprise performing purification and/or identification technologies. In various embodiments, isolating the sample from the cleavage by-products may comprise at least one of reversed phase sample clean-up techniques and solid phase extraction techniques. In various embodiments, isolating the sample from the cleavage by-products may be selected from the group consisting of ion exchange, hydrophilic interaction, reversed phase chromatographic preparations, and any combination thereof.

In various embodiments the method of isolating a sample may comprise performing electrokinetic transport of the sample-surfactant complex. In at least one embodiment, performing electrokinetic transport may comprise electrophoresis. In at least one embodiment, electrophoresis may comprise gel electrophoresis, free zone electrophoresis, and capillary electrophoresis. In at least one embodiment, electrophoresis may comprise polyacrylamide gel electrophoresis, including the tube, slab gel and capillary formats of polyacrylamide gel electrophoresis. In at least one embodiment, electrophoresis may comprise two-dimensional electrophoresis, such as, for example, 2D SDS-PAGE. In various embodiments, the compound may suppress electroosmotic flow (EOF) in CE capillaries and/or microfluidic devices. For example, the surfactant may be added to an electrophoresis buffer solution. The surfactant may interact with inner surface of a fused silica capillary to suppress EOF.

In various embodiments the method of isolating a sample may comprise purifying the isolated sample. In various embodiments, purifying may comprise conventional separation methods, including, but not limited to, liquid-liquid extraction, solid-phase extraction and liquid chromatography.

In various embodiments the method of isolating a sample may comprise performing enzymatic digestion of the sample-surfactant complex. In various embodiments, performing enzymatic digestion may comprise forming a sample-surfactant complex by contacting a sample and an acid-labile surfactant according to Formula II (final concentration of 0.01-

1.0%) in a buffered solution of 10-100 mM ammonium bicarbonate; incubating the sample-surfactant complex with dithiothreitol (DTT) (5-50 mM) for less than one (1) hour at 50-60° C. for reduction of cysteine-cysteine disulfide linkages; cooling the sample-surfactant complex mixture; incubating the sample-surfactant complex mixture with iodoacetamide (25-250 mM) for less than one (1) hour at less than 30° C. in limited light; mixing the sample-surfactant complex with an enzyme; and incubating the mixture for less than 24 hours at 20-40° C. with shaking. In various embodiments, performing enzymatic digestion may comprise incubating the sample-surfactant complex in 50 mM ammonium bicarbonate for 30 minutes at 55° C. with 5 mM DTT; cooling the sample-surfactant complex to room temperature; incubating the sample-surfactant complex for 30 minutes at room temperature in the dark in 25 mM iodoacetamide; mixing the sample-surfactant complex with an enzyme; and incubating the mixture for 4-12 hours at 37° C. with shaking. In various embodiments, the enzyme may be selected from the group consisting of trypsin, Arg-C, Lys-C, Asp-N, chymotrypsin, and pepsin.

In various embodiments, performing enzymatic digestion may comprise incubating the sample-surfactant complex for less than one (1) hour at less than 99° C.; cooling the sample-surfactant complex; incubating the sample-surfactant complex for less than one (1) hour at less than 99° C. in limited light; mixing the sample-surfactant complex with an enzyme; and incubating the mixture for less than 12 hours at 4-55° C. with shaking. In various embodiments, performing enzymatic digestion may comprise incubating the sample-surfactant complex for 30 minutes at 55° C.; cooling the sample-surfactant complex to room temperature; incubating the sample-surfactant complex for 30 minutes at room temperature in the dark; mixing the sample-surfactant complex with an enzyme; and incubating the mixture for 4-8 hours at 37° C. with shaking.

In various embodiments the method of isolating a sample may further comprise desalting the sample-surfactant complex with an enzyme. In at least one embodiment, desalting may comprise cleaving the sample-surfactant complex. In at least one embodiment, desalting may comprise degrading the surfactant of the sample-surfactant complex. In various embodiments, desalting may comprise loading the mixture of the sample and degraded surfactant onto a solid phase extraction chromatographic media; washing away the salts and surfactant degradation products, and collecting the sample from the solid phase extraction media by elution. In various embodiments, the solid phase extraction media may be selected from the group consisting of reversed phase, ion exchange, hydrophilic interaction (HILIC), and any combination thereof.

In various embodiments, a method for analyzing a sample may generally comprise contacting a sample with a non-ionic acid-labile surfactant according to Formula II to form a sample-surfactant complex and analyzing the sample-surfactant complex. In various embodiments, analyzing may comprise purification and/or identification technologies. In various embodiments, analyzing may comprise at least one of electrophoresis, electroelution, high performance liquid chromatography, mass spectrometric detection, liquid-liquid extraction, solid phase extraction, and ion-pair liquid chromatography. In at least one embodiment, the method for analyzing a sample may generally comprise degrading the surfactant. In at least one embodiment, the method for analyzing a sample may generally comprise purifying the sample after degrading the surfactant.

In various embodiments, a method for performing electrophoresis may generally comprise contacting a sample with a non-ionic acid-labile surfactant according to Formula II to form a sample-surfactant complex, performing electrophoresis on the sample-surfactant complex, and degrading the surfactant after electrophoresis. In at least one embodiment, degrading may comprise contacting the surfactant with an acidic solution. In at least one embodiment, degrading may comprise contacting the surfactant with an acid with the proviso that the acid is not a strong acid. In at least one embodiment, the method for performing electrophoresis may generally comprise purifying the sample after degrading the surfactant.

F. Examples

The various embodiments of non-ionic acid-labile surfactants and methods of use described herein may be better understood when read in conjunction with the following representative examples. The following examples are included for purposes of illustration and not limitation. MALDI-TOF spectra were acquired using an ABI 4800 mass spectrometer in the linear mode.

Referring to FIGS. 1A-C, 0.1% N-[2,2-Bis(pentyloxy)propan-1-aminocarbonyl]-β-maltosylamine was mixed with myoglobin in water. The samples were spotted onto a MALDI pre-spotted target with α-cyano-4-hydroxycinnamic acid (CHCA) MALDI matrix using C8 reversed phase tips. FIG. 1A includes a mass spectra of 20 pmol myoglobin in water. Myoglobin was detected at m/z 8488 and m/z 16979. FIG. 1B includes a mass spectra of 20 pmol myoglobin dissolved in 0.1% N-[2,2-Bis(pentyloxy)propan-1-aminocarbonyl]-β-maltosylamine. Without wishing to be bound to any particular theory, it is believed that no signal from the myoglobin was detected because the myoglobin was associated with the surfactant. FIG. 1C includes a mass spectra of 20 pmol myoglobin dissolved in 0.1% N-[2,2-Bis(pentyloxy)propan-1-aminocarbonyl]-β-maltosylamine after being degraded for about thirty (30) minutes in 1% trifluoroacetic acid (TFA) at pH 2.5. Myoglobin was detected at m/z 8482 and m/z 16967. As shown in FIGS. 1B and 1C, a signal from the myoglobin was detected when the surfactant was degraded. Without wishing to be bound to any particular theory, it is believed that the myoglobin was detected at greater signal intensities than FIG. 1A because the surfactant improved the myoglobin's solubility.

Figure 2B:
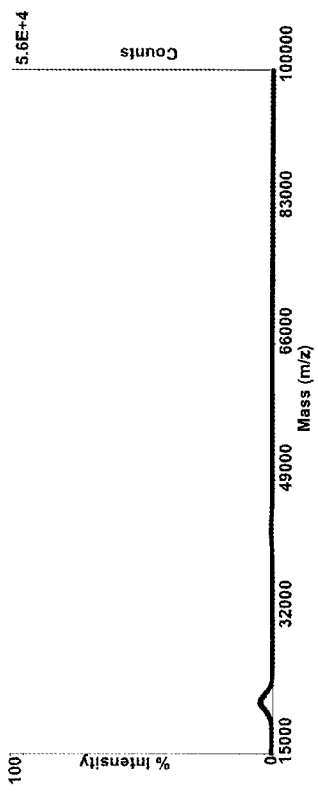
Figure 2C:
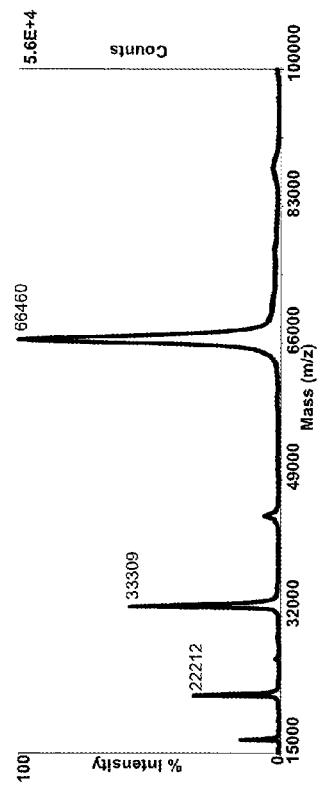

Referring to FIGS. 2A-C, 0.1% N-[2,2-Bis(pentyloxy)propan-1-aminocarbonyl]-β-maltosylamine was mixed with bovine serum albumin (BSA) in water. The samples were spotted onto a MALDI pre-spotted target with CHCA MALDI matrix using C8 reversed phase tips. FIG. 2A includes a mass spectra of 20 pmol BSA in water. BSA was detected at m/z 22344, m/z 33480, and m/z 66854. FIG. 2B includes a mass spectra of 20 pmol BSA dissolved in 0.1% N-[2,2-Bis(pentyloxy)propan-1-aminocarbonyl]-β-maltosylamine. Without wishing to be bound to any particular theory, it is believed that no signal from the BSA was detected because the BSA was associated with the surfactant. FIG. 2C includes a mass spectra of 20 pmol BSA in 0.1% N-[2,2-Bis(pentyloxy)propan-1-aminocarbonyl]-β-maltosylamine after being degraded for about thirty (30) minutes in 1% TFA at pH 2.5. BSA was detected at m/z 22212, m/z 33309, and m/z 66460. As shown in FIGS. 2B and 2C, a signal from the BSA was detected when the surfactant was degraded.

Figure 3A:
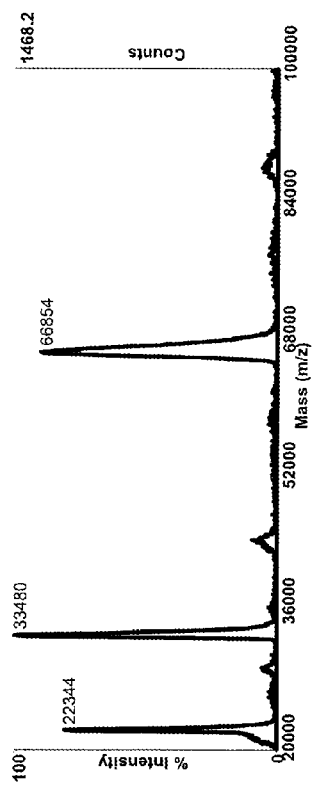
FIGS. 3A-C illustrate representative mass spectra of BSA according to certain embodiments.
Figure 3B:
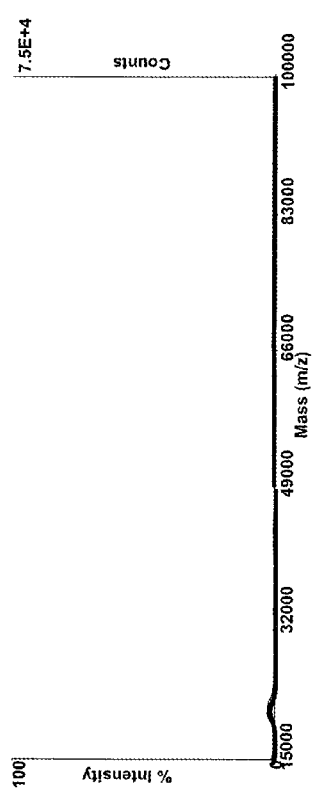
Figure 3C:
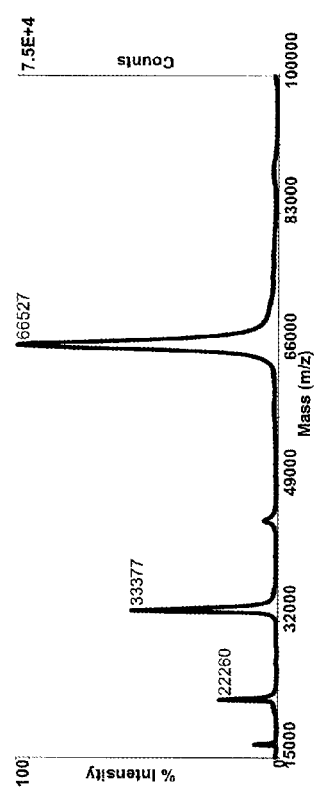

Referring to FIGS. 3A-C, 1% N-[2,2-Bis(pentyloxy)propan-1-aminocarbonyl]-β-maltosylamine was mixed with bovine serum albumin (BSA) in water. The samples were spotted onto a MALDI pre-spotted target with CHCA MALDI matrix using C8 reversed phase tips. FIG. 3A includes a mass spectra of 20 pmol BSA in water. BSA was detected at m/z 22344, m/z 33480, and m/z 66854. FIG. 3B includes a mass spectra of 20 pmol BSA dissolved in 1% N-[2,2-Bis(pentyloxy)propan-1-aminocarbonyl]-β-maltosylamine. Without wishing to be bound to any particular theory, it is believed that no signal from the BSA was detected because the BSA was associated with the surfactant. FIG. 3C includes a mass spectra of 20 pmol BSA in 1% N-[2,2-Bis(pentyloxy)propan-1-aminocarbonyl]-β-maltosylamine after being degraded for about thirty (30) minutes in 1% TFA at pH 2.5. BSA was detected at m/z 22260, m/z 33377, and m/z 66527. As shown in FIGS. 3B and 3C, a signal from the BSA was detected when the surfactant was degraded.

Referring to FIGS. 4A-C 1% N-[2,2-Bis(hexyloxy)propan-1-aminocarbonyl]-β-maltosylamine was mixed with myoglobin. The samples were spotted onto a MALDI pre-spotted target with α-cyano-4-hydroxycinnamic acid (CHCA) MALDI matrix using C8 reversed phase tips. FIG. 5A includes a mass spectra of 20 pmol myoglobin in water. Myoglobin was detected at m/z 8488 and m/z 16979. FIG. 4B includes a mass spectra of 20 pmol myoglobin dissolved in 1% N-[2,2-Bis(hexyloxy)propan-1-aminocarbonyl]-β-maltosylamine. Without wishing to be bound to any particular theory, it is believed that no signal from the myoglobin was detected because the myoglobin was associated with the surfactant. FIG. 5C includes a mass spectra of 20 pmol myoglobin dissolved in 1% N-[2,2-Bis(hexyloxy)propan-1-aminocarbonyl]-β-maltosylamine after being degraded for about thirty (30) minutes in 1% trifluoroacetic acid (TFA) at pH 2.5. Myoglobin was detected at m/z 8492 and m/z 16986. As shown in FIGS. 4B and 4C, a signal from the myoglobin was detected when the surfactant was degraded. Without wishing to be bound to any particular theory, it is believed that the myoglobin was detected at greater signal intensities than FIG. 4A because the surfactant improved the myoglobin's solubility.

Referring to FIGS. 5A-C, 0.1% N-[2,2-Bis(hexyloxy)propan-1-aminocarbonyl]-β-maltosylamine was mixed with BSA. The samples were spotted onto a MALDI pre-spotted target with CHCA MALDI matrix using C8 reversed phase tips. FIG. 5A includes a mass spectra of 20 pmol BSA in water. BSA was detected at m/z 22344, m/z 33480, and m/z 66854. FIG. 5B includes a mass spectra of 20 pmol BSA dissolved in 0.1% N-[2,2-Bis(hexyloxy)propan-1-aminocarbonyl]-β-maltosylamine. Without wishing to be bound to any particular theory, it is believed that no signal from the BSA was detected because the BSA was associated with the surfactant. FIG. 5C includes a mass spectra of 20 pmol BSA in 0.1% N-[2,2-Bis(phexyloxy)propan-1-aminocarbonyl]-β-maltosylamine after being degraded for about thirty (30) minutes in 1% TFA at pH 2.5. BSA was detected at m/z 22197, m/z 33284, and m/z 66405. As shown in FIGS. 5B and 5C, a signal from the BSA was detected when the surfactant was degraded.

The non-ionic acid-labile surfactant may improve the sensitivity of mass spectrometry analysis of proteins in the presence of the degraded non-ionic acid-labile surfactants. Cleavage of these non-ionic acid-labile surfactants may reduce or eliminate the detergent properties that induce signal suppression and/or create signal adducts in the mass spectra. Adduct peaks in mass spectra may result from a population of surfactant-protein complexes containing different numbers of surfactant molecules per protein, resulting in many different complexes (with different masses) to be detected. If there is no surfactant present to form a surfactant-protein complex, then these adducts may not be formed or observed. This mechanism demonstrates the utility for removing surfactants by cleavage to improve mass spectrometry analysis. These effects may increase the signal intensity of analytes and/or eliminate the suppressive effects of conventional detergents.

All documents cited herein are incorporated herein by reference, but only to the extent that the incorporated material does not conflict with existing definitions, statements, or other documents set forth herein. To the extent that any meaning or definition of a term in this document conflicts with any meaning or definition of the same term in a document incorporated by reference, the meaning or definition assigned to that term in this document shall govern. The citation of any document is not to be construed as an admission that it is prior art with respect to the non-ionic acid-labile surfactants and methods of use described herein.

While particular exemplary embodiments of non-ionic acid-labile surfactants and methods of use have been illustrated and described, it would be obvious to those skilled in the art that various other changes and modifications can be made without departing from the spirit and scope of the invention. Those skilled in the art will recognize, or be able to ascertain using no more than routine experimentation, numerous equivalents to the specific devices and methods described herein, including alternatives, variants, additions, deletions, modifications and substitutions. This disclosure, including the claims, is intended to cover all such equivalents that are within the spirit and scope of this invention.

What is claimed is:

1. A compound of the formula:

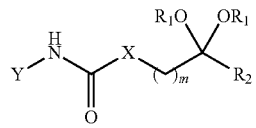

wherein $R_1$ is selected from —$(CH_2)_{2-7}CH_3$ alkyl, $R_2$ is selected from —$(CH_2)_{0-2}CH_3$ alkyl, X is selected from the group consisting of —NH— and —O—, Y is a sugar, and m is an integer from 1 to 4.

2. A compound of the formula:

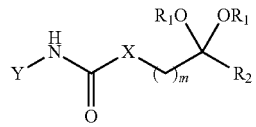

wherein $R_1$ is selected from —$(CH_2)_{2-7}CH_3$ alkyl, $R_2$ is selected from —$(CH_2)_{0-2}CH_3$ alkyl, X is selected from the group consisting of —NH— and —O—, Y is selected from the group consisting of a monosaccharide, a disaccharide, an oligosaccharide, and a polysaccharide, and m is an integer from 1 to 4.

3. The compound of claim 1, wherein $R_1$ is selected from —$(CH_2)_{2-7}CH_3$ alkyl, $R_2$ is —$CH_3$, Y is a monosaccharide, and m is 1.

4. The compound of claim 1, wherein $R_1$ is selected from —$(CH_2)_{2-7}CH_3$ alkyl, $R_2$ is —$CH_3$, Y is a disaccharide, and m is 1.

5. The compound of claim 1, wherein $R_1$ is selected from —$(CH_2)_{2-7}CH_3$ alkyl, $R_2$ is —$CH_3$, Y is a trisaccharide, and m is 1.

6. The compound of claim 1, wherein $R_1$ is selected from —$(CH_2)_{2-7}CH_3$ alkyl, $R_2$ is —$CH_3$, Y is a tetrasaccharide, and m is 1.

7. The compound of claim 1, wherein Y is one of a disaccharide, an oligosaccharide, and a polysaccharide comprising a cellobiose unit, a galactose unit, a glucose unit, a glucosamine unit, a fructose unit, a lactose unit, a maltose unit, a mannose unit, a sucrose unit, and combinations thereof.

8. The compound of claim 1, wherein $R_1$ is selected from —$(CH_2)_{2-7}CH_3$ alkyl, $R_2$ is —$CH_3$, Y is a disaccharide comprising a maltose unit, and m is 1.

9. The compound of claim 1, wherein $R_1$ is selected from —$(CH_2)_{2-7}CH_3$ alkyl, $R_2$ is —$CH_3$, Y is a disaccharide comprising a glucose unit, and m is 1.

10. The compound of claim 1, wherein $R_1$ is selected from —$(CH_2)_{2-7}CH_3$ alkyl, $R_2$ is —$CH_3$, Y is a disaccharide comprising glucose units, and m is 1.

11. The compound of claim 1, wherein X is —NH—.

12. The compound of claim 1, wherein X is —O—.

13. The compound of claim 1 comprising N-[2,2-Bis(pentyloxy)propan-1-aminocarbonyl]-β-maltosylamine having the formula:

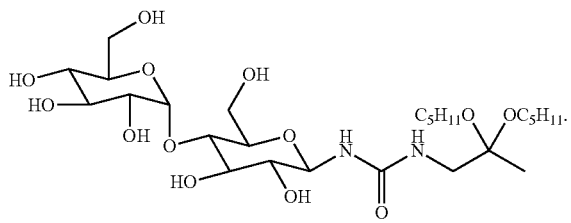

14. The compound of claim 1 comprising N-[2,2-Bis(hexyloxy)propan-1-aminocarbonyl]-β-maltosylamine having the formula:

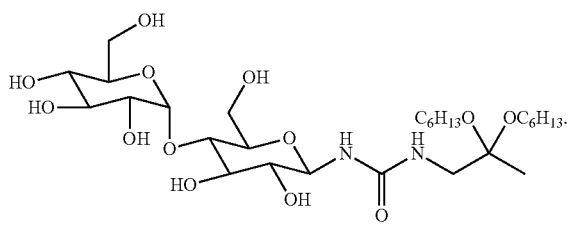

15. The compound of claim 1 comprising N-[2,2-Bis(pentloxy)propan-1-oxycarbonyl]-β-maltosylamine having the formula:

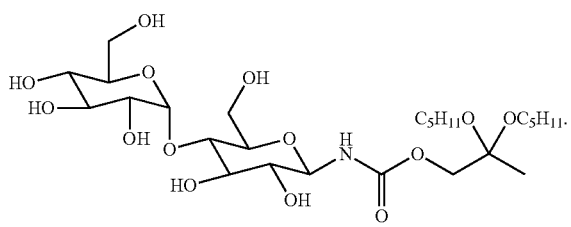

16. The compound of claim 1 comprising N-[2,2-Bis(hexyloxy)propan-1-oxycarbonyl]-β-maltosylamine having the formula:

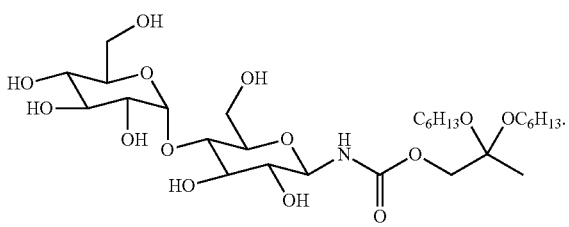

17. The compound of claim 1 having the formula:

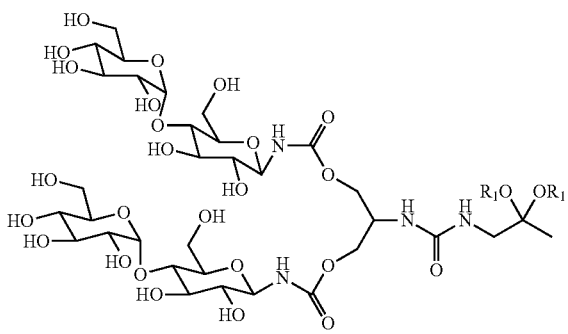

wherein $R_1$ may be independently selected from $C_2$-$C_{10}$ alkyl or substituted alkyl.

18. The compound of claim 1 having the formula:

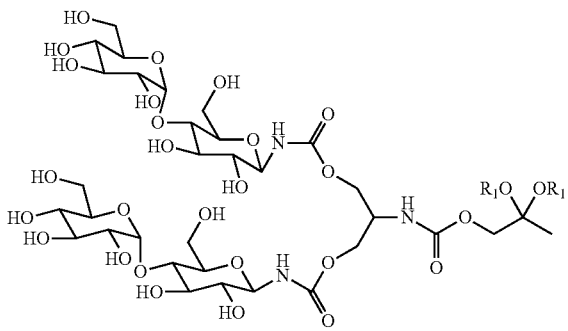

wherein $R_1$ may be independently selected from $C_2$-$C_{10}$ alkyl or substituted alkyl.

19. A non-ionic acid labile surfactant having the formula of claim 1.

20. A non-ionic acid labile surfactant having the formula of claim 2.

* * * * *